United States Patent
Bendek et al.

(10) Patent No.: US 10,179,206 B2
(45) Date of Patent: Jan. 15, 2019

(54) MEDICAMENT DELIVERY DEVICE

(71) Applicant: CAREBAY EUROPE LTD, Sliema (MT)

(72) Inventors: Antonio Bendek, Wellington, FL (US); Lucio Giambattista, Lighthouse Point, FL (US)

(73) Assignee: SHL MEDICAL AG, Zug (CH)

( * ) Notice: Subject to any disclaimer, the term of this patent is extended or adjusted under 35 U.S.C. 154(b) by 86 days.

(21) Appl. No.: 15/307,905

(22) PCT Filed: Apr. 10, 2015

(86) PCT No.: PCT/EP2015/057827
§ 371 (c)(1),
(2) Date: Oct. 31, 2016

(87) PCT Pub. No.: WO2015/165718
PCT Pub. Date: Nov. 5, 2015

(65) Prior Publication Data
US 2017/0056592 A1 Mar. 2, 2017

Related U.S. Application Data

(60) Provisional application No. 61/987,707, filed on May 2, 2014.

(30) Foreign Application Priority Data

Apr. 11, 2014 (SE) ....................................... 1451313

(51) Int. Cl.
*A61M 5/20* (2006.01)
*A61M 5/31* (2006.01)
(Continued)

(52) U.S. Cl.
CPC ........ *A61M 5/2066* (2013.01); *A61M 5/2033* (2013.01); *A61M 5/3146* (2013.01); *A61M 5/31501* (2013.01); *A61M 5/2448* (2013.01)

(58) Field of Classification Search
CPC .............. A61M 5/2033; A61M 5/2066; A61M 5/3156; A61M 5/31501
See application file for complete search history.

(56) References Cited

U.S. PATENT DOCUMENTS 4,236,516 A * 12/1980 Nilson .................... A61J 1/062
604/214
8,123,719 B2 2/2012 Edwards et al.
(Continued)

FOREIGN PATENT DOCUMENTS

WO 2012/030277 3/2012
WO WO-2012/030276 * 3/2012 ........ A61M 5/31515

OTHER PUBLICATIONS

International Search Report and Written Opinion for Int. App. No. PCT/EP2015/057827, dated Sep. 28, 2015.

*Primary Examiner* — Emily Schmidt
(74) *Attorney, Agent, or Firm* — McDonnell Boehnen Hulbert & Berghoff LLP

(57) ABSTRACT

A medicament delivery device is presented having a housing, and a medicament container holder arranged movable in a longitudinal direction in relation to the housing. The medicament container holder is arranged to accommodate a medicament container, is arranged as a multi-chamber container having a medicament and a diluent in different chambers, a plunger rod operably arranged to act on the medicament container, a retaining element capable of releasably retaining the plunger rod to the housing, actuation force elements capable of, upon activation, moving the medicament container holder in relation to the housing such that the
(Continued)

plunger rod acts on the medicament container for mixing the medicament and the diluent.

11 Claims, 13 Drawing Sheets

(51) Int. Cl.
*A61M 5/315* (2006.01)
*A61M 5/24* (2006.01)

(56) References Cited

U.S. PATENT DOCUMENTS

| | | |
|---|---|---|
| 8,323,238 B2 | 12/2012 | Cronenberg et al. |
| 2012/0053516 A1* | 3/2012 | Cronenberg ........ A61M 5/2033 604/82 |
| 2012/0123350 A1* | 5/2012 | Giambattista ....... A61M 5/2033 604/198 |

* cited by examiner

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2015/057827 filed Apr. 10, 2015, which claims priority to U.S. Provisional Patent Application No. 61/987,707 filed May 2, 2015 and Swedish Patent Application No. 1451313-9, filed Nov. 4, 2014. The entire disclosure contents of these applications are herewith incorporated by reference into the present application.

TECHNICAL AREA

The present invention relates to a medicament delivery device capable of providing a function in which a dual chamber medicament container is handled in an efficient way without unnecessarily increasing the size of the device.

BACKGROUND

There are liquid medicament compositions that degrade and lose their potency over time, before they can be administered to a patient.

In order to handle these medicament compositions, so called multi chamber medicament containers have been developed. They often comprise elongated tubular containers divided by movable stoppers into a number of compartments or chambers, where the medicament in powder form is placed in one chamber and a diluent is placed in another chamber. At certain positions along the containers, passages are arranged, wherein, when the stoppers are moved, the passages are opened, allowing communication between the chambers and thus a mixing between the medicament and the diluent. The stoppers are often moved by an elongated plunger rod, which is often actuated by a drive spring.

After mixing, a priming sequence is often necessary, in which air and gas entrapped in the medicament container after mixing needs to be removed. The stoppers have to be moved a short distance by the plunger rod in order to remove the air. The injection sequence is performed after mixing and priming.

One problem with devices handling dual chamber medicament containers is that the devices tend to be rather long because the plunger rods have to be moved in the longitudinal direction of the devices both for priming, mixing and injection if the same drive springs are to be used for all the sequences. Also, a mechanical solution allowing the plunger rod to be actuated and stopped at several instances usually requires rather complex mechanisms.

The document U.S. Pat. No. 8,323,238 discloses a medicament delivery device arranged to handle multi-chamber containers. However it contains only one drive spring and will therefore be rather long. Its length is not altered during use of the device.

The document U.S. Pat. No. 8,123,719 discloses a medicament delivery device employing several drive springs in order to perform different required functions. However, the device is bulky and not intended for personal use by patients without medical training.

SUMMARY

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The aim of the present invention is to remedy the drawbacks of the state of the art devices. This aim is obtained with a medicament delivery device according to the independent patent claim. Preferable embodiments of the invention form the subject of the dependent patent claims.

The medicament delivery device according to the invention comprises a housing. The housing is connected to a medicament container holder arranged movable in a longitudinal direction in relation to the housing. The medicament container holder is preferably arranged to accommodate a medicament container. The medicament container may be of a number of different types suitable for containing and delivering doses of medicament, but in the preferred solution the medicament container is arranged as a multi-chamber container comprising medicament and diluent in separate chambers.

The medicament delivery device may further preferably comprise a plunger rod operably arranged to act on the medicament container. The plunger rod is preferably elongated and sized to fit into the medicament container. The medicament delivery device may further be arranged with a retaining element capable of releasably retaining the plunger rod in relation to the housing.

According to a favourable solution actuation force elements are arranged and capable of, upon activation, moving said medicament container holder in relation to said housing such that said plunger rod acts on said medicament container for mixing said medicament and said diluent. With this solution, the plunger rod does not move when a mixing sequence is performed. Instead the medicament container is moved in the distal direction of the device in relation to the plunger rod. Thus the drive force elements are separated from any drive elements usually connected and operable on the plunger rod. Further the device becomes considerably shorter after the mixing sequence.

According to another favourable solution, the medicament delivery device may further comprise a drive force element operably connected to the plunger rod such that, when said retaining element is actuated for releasing the plunger rod, it is forced to act on the medicament container for expelling the mixed medicament through a medicament delivery member. Thus, a separate drive force element is arranged for the dose delivery sequence. This shortens the length of the device because two separate force elements are used for different operation sequences.

Preferably, the plunger rod may comprise first stop elements co-acting with the retaining element and capable of holding the plunger rod in an initial position, and as well as second stop elements capable of stopping the plunger rod after a first distance in the longitudinal direction for performing mixing. The mixing sequence is thus performed and the plunger rod is stopped until the next sequence is to be performed.

In that respect the plunger rod may comprise third stop elements capable of stopping the plunger rod after a second distance in the longitudinal direction for performing priming. Thus also a priming step is performed and the plunger rod is stopped until the next sequence is to be performed.

In order to obtain said functions, the stop elements may comprise stop ledges arranged on an outer surface of the plunger rod, which stop ledges are arranged generally transversal to the longitudinal direction, where the stop ledges are arranged to interact with stop surfaces on the medicament container holder. Thus the outer surface of the plunger rod is used for realising the desired functional sequences.

Further the stop surfaces may comprise fixed ledges arranged to move in longitudinally extending groove sections on the outer surface of said plunger rod. In that respect groove sections may be placed offset to each other in a circumferential direction of said plunger rod, and wherein an end surface of a groove section comprises said stop ledges. The grooves are readily obtained on the outer surface and when the grooves are arranged offset to each other the end surfaces of the grooves become natural stop ledges.

The plunger rod may be rotatable relative to the container holder in order to shift the fixed ledges from one groove section to a subsequent groove section. A user may, for instance, rotate the plunger rod by turning an knob, arranged on the medicament delivery device.

Further, the medicament delivery device may comprise a manually operable activation element, operably connected to said retaining element for releasing said plunger rod when activated. The retaining element may comprise ledges arranged to fit into a groove segment of said plunger rod and to contact a stop ledge for holding said plunger rod.

Also, the manually operable activation element may comprise release elements operably arranged to move said ledges of said retaining element out of contact with said stop ledge for releasing said plunger rod.

BRIEF DESCRIPTION OF DRAWINGS

In the following detailed description of the invention, reference will be made to the accompanying drawings, of which

DETAILED DESCRIPTION

Figure 2:
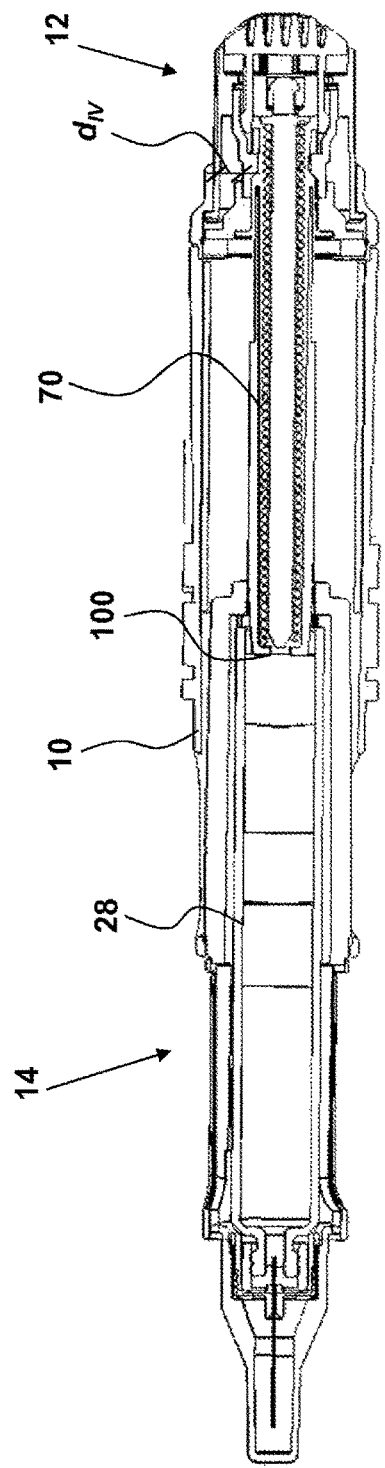
FIG. 2 is a longitudinal cross-sectional view of the device of FIG. 1, FIGS. 3-7 are detailed views of components comprised in the medicament delivery device of FIG. 1, and FIGS. 8-13 are detailed functional views of different steps.
Figure 3:
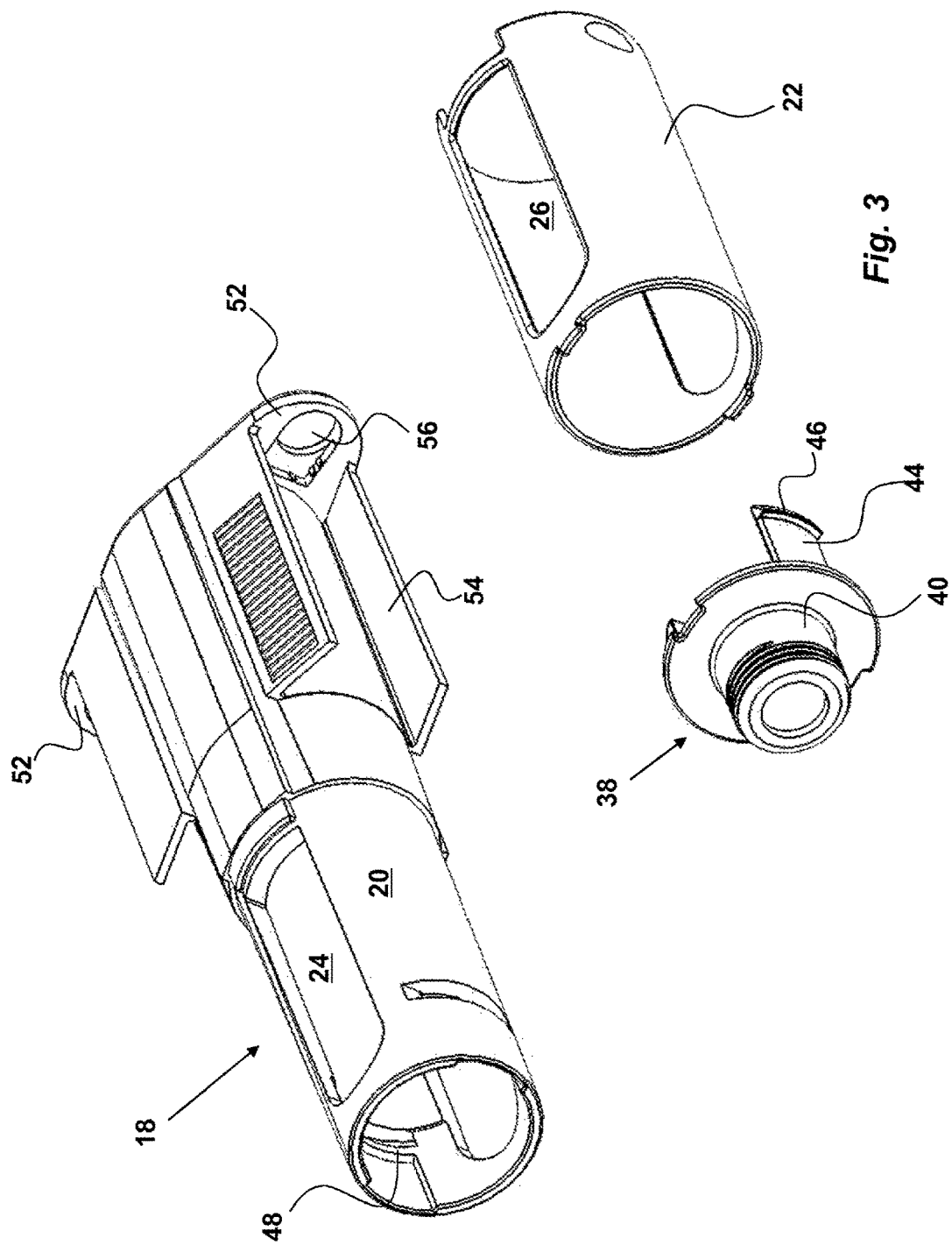

The medicament delivery device shown in the drawings comprises a housing 10, FIG. 2, having a distal end 12 and a proximal end 14. At the proximal end a central passage 16 is arranged, FIG. 2b. In the central passage 16 a generally tubular medicament container holder 18, FIG. 2b, extends in the proximal direction. The proximal part 20 of the medicament container holder 18, FIG. 3, is surrounded by a coaxial retainer sleeve 22. Both the medicament container holder 18 and the retainer sleeve 22 are arranged with windows or openings 24 and 26, through which a medicament container 28 may viewed. In the embodiment shown the medicament container 28 is a so called dual chamber container wherein a first chamber 30 is contains a medicament in dry form while the second chamber 32 contains diluent. The chambers are separated by a first movable stopper 34. Further the distal end of the medicament container is arranged with a second movable stopper 36.

The medicament container is retained in the medicament container holder by a medicament container retainer 38 attached to the proximal end thereof such that the neck of the medicament container may extend through a tubular neck 40 of the medicament container retainer 38. The neck 40 is arranged with suitable fastening elements capable of cooperating with mating fastening elements arranged on a medicament delivery member 42, FIG. 2. The fastening elements could comprise threads as shown, or bayonet connections or luer connections, just to mention a few. The medicament container retainer 38 is attached to the medicament container by distally directed tongues 44 extending into the medicament container holder. The free ends of the tongues 44 are arranged with outwardly extending ledges 46, which ledges 46 are arranged to fit into and lock with grooves 48 on an inner surface of the medicament container holder 18, FIG. 3.

Figure 4:
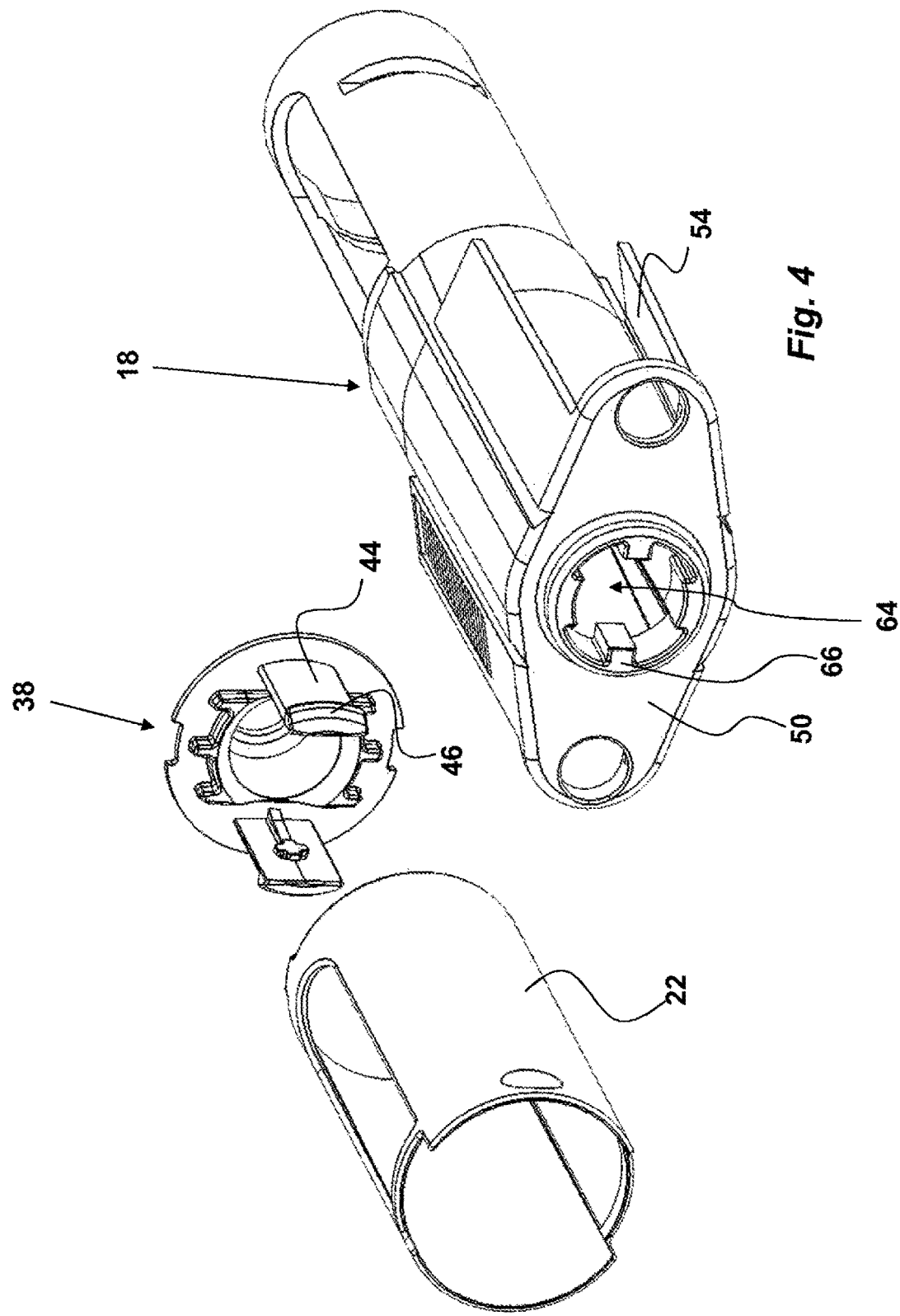

At the distal end of the medicament container holder 18 an end plate 50, FIG. 4, is attached or made integral with the medicament container holder. The end plate 50 extends generally transversally with two oppositely positioned support plates 52, FIG. 3. These support plates 52 are in turn made rigid with support walls 54 extending in the proximal direction and attached to the support plates 52 as well as to the outer side surface of the medicament container holder 18. The support plates 52 are further arranged with through holes 56, in which attachment posts of guide rods 58 for actuation force elements 60 may be attached, FIGS. 1 and 2. These elements 60 are in the embodiment shown two compression springs that are tensioned between the end plates 52 and a distally directed wall surface 62 of the housing 10, FIG. 2b.

Figure 5:
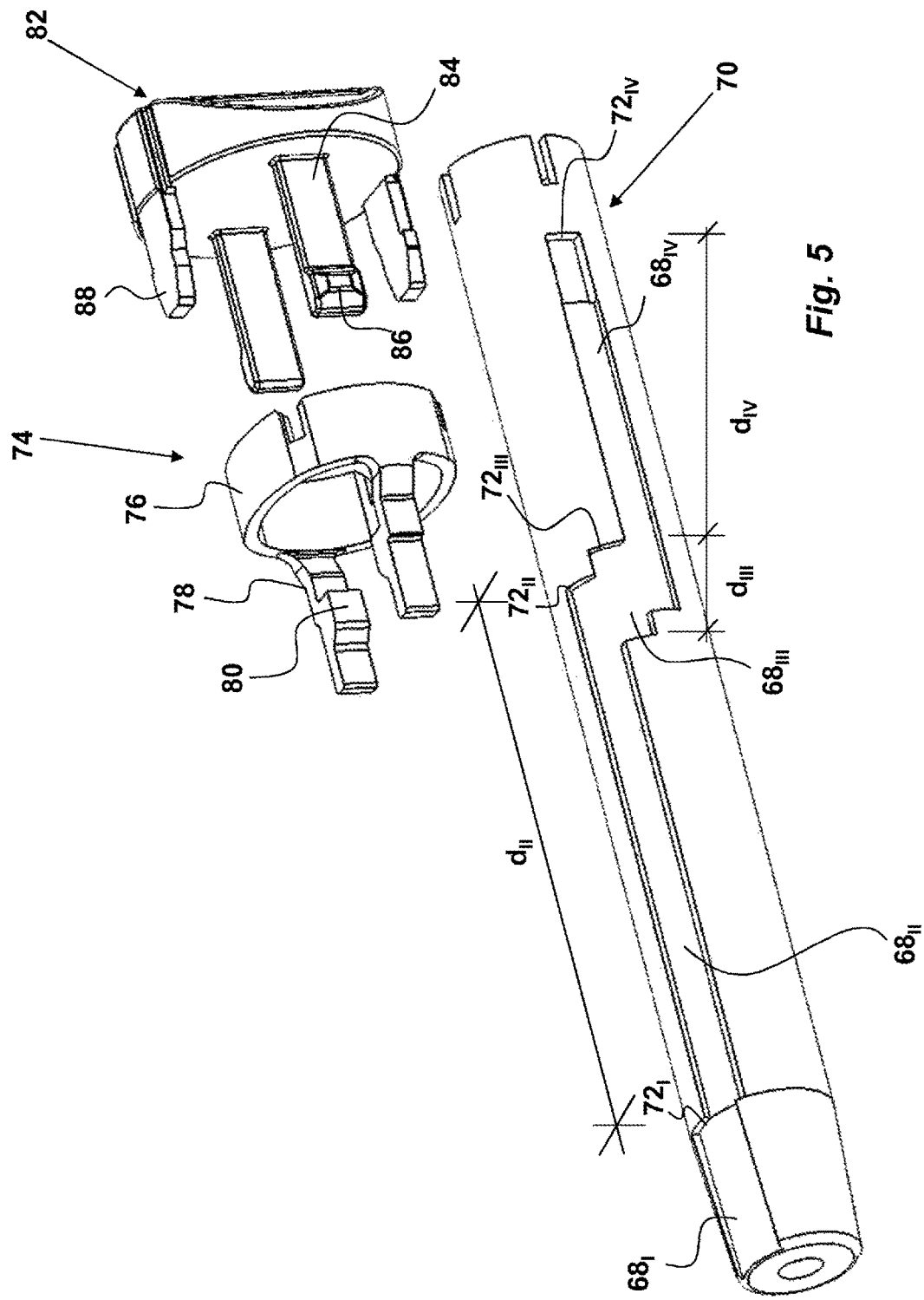

Further the distal end of the medicament container holder 18 is arranged with a central passage 64, FIG. 4. The central passage 64 is arranged with radially inwardly directed, generally rectangular ledges 66. These ledges 66 are intended to cooperate with longitudinal grooves 68 of a plunger rod 70, FIG. 5. The plunger rod 70 is arranged to extend into the medicament container holder 18 and to act on the second stopper 38 as seen in FIG. 2b. Further, as seen in FIG. 5, the grooves of the plunger rod are divided into sections. A first section $68_I$ at the proximal end of the plunger rod 70 ends with a proximally directed first stop ledge $72_I$. A second section $68_{II}$ is connected to the first section $68_I$ and arranged offset in the circumferential direction in relation to the first section $68_I$. The second section $68_{II}$ ends with a proximally directed second stop ledge $72_{II}$ at a distance $d_{II}$, from the first stop ledge $72_I$, along the plunger rod 70. A third section $68_{III}$ connects to the second section $68_{II}$. The third section $68_{III}$ is arranged offset in relation to the second section. The third section $68_{III}$ has a shorter distance $d_{III}$ in relation to the second section $68_{II}$ and ends with a third stop ledge $72_{III}$. A fourth section $68_{IV}$ connects to the third section $68_{III}$, positioned offset in the circumferential direction. The fourth section $68_{IV}$ ends at a distance $d_{IV}$ at the distal end of the plunger rod 70 with a fourth stop ledge $72_{IV}$.

Further, a retaining element in the form of a release tab 74, FIG. 5, is provided that is intended to interact with the grooves 68 of the plunger rod and in particular the fourth section $68_{IV}$ and its stop ledge $72_{IV}$ as will be described below. The release tab 74 has a generally ring-shaped body 76 with two arms 78 extending in the proximal direction, where the arms 78 are positioned opposite each other on the body 76. The arms 78 are further arranged with radially inwardly directed ledges 80 that are arranged to fit into the fourth section 68IV of the grooves. In that position of the arms 78 there is a distance $d_V$, FIG. 2a, in the radial direction to the inner wall of the housing 10. Further, an activation element in the form of a push button 82, FIG. 5, is arranged distally of the release tab 74. The push button 82 is arranged with two proximally extending arms 84. The free ends of the arms 84 are arranged with generally outwardly directed protrusions 86, which protrusions are arranged to be in contact with inner surfaces of the arms 78 of the release tab 74. The push button is further arranged with two guide arms 88 extending in the proximal direction.

Figure 1:
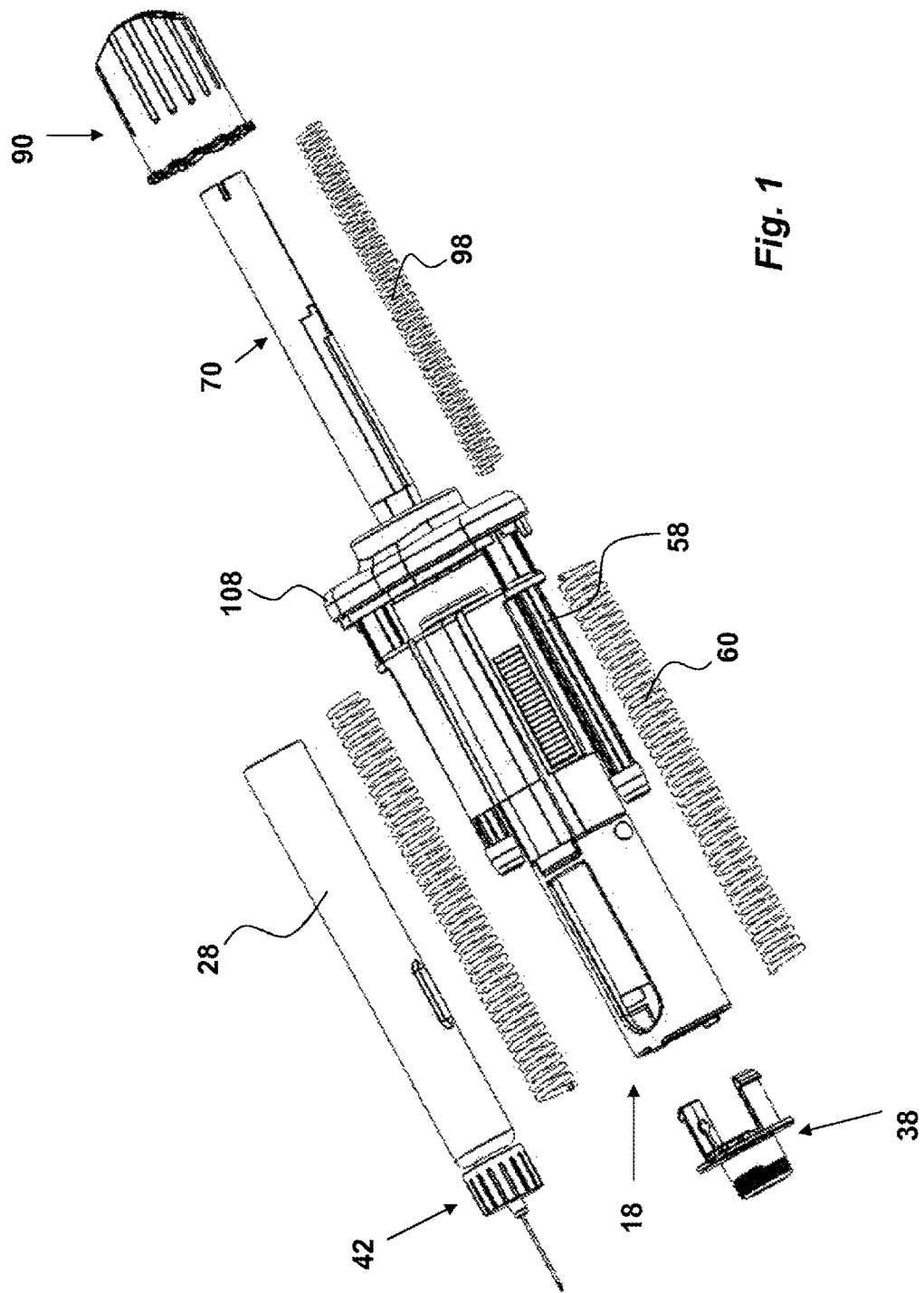
FIG. 1 is an exploded view of a medicament delivery device.
Figure 6:
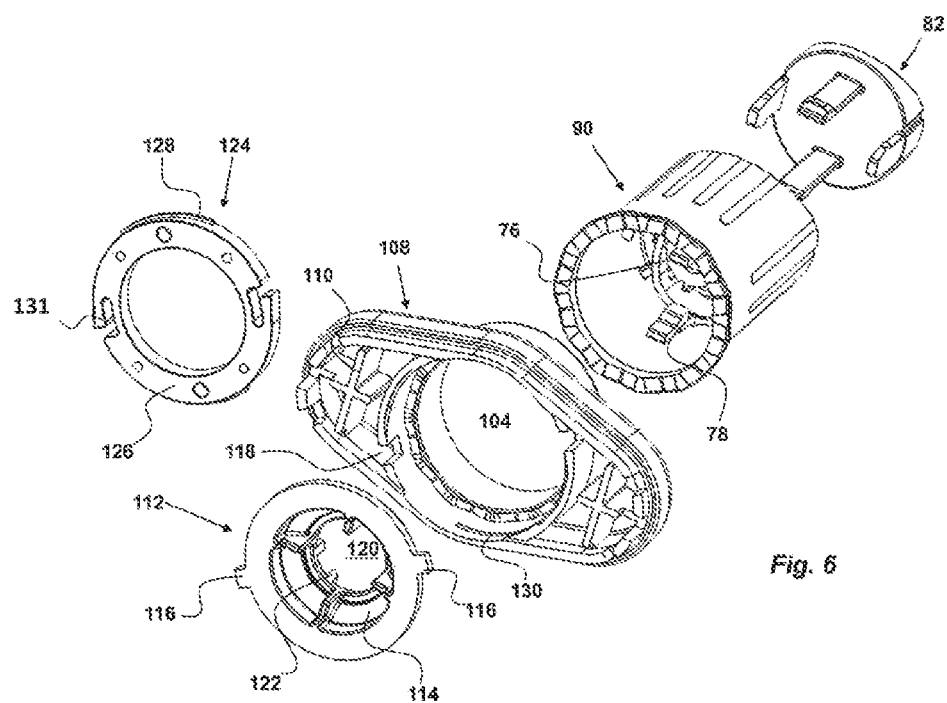
Figure 7:
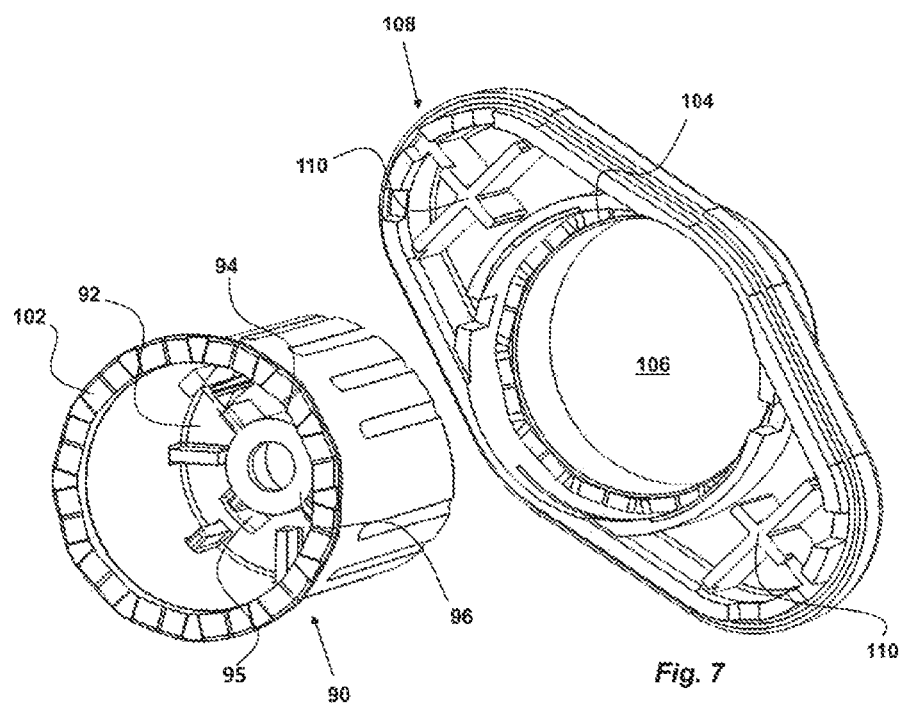

Both the release tab 74 and the push button 82 are arranged in a generally tubularly shaped knob 90, FIG. 6, arranged at the distal end of the medicament delivery device. The knob 90 is arranged with a generally transversal end wall 92, FIG. 7. The end wall 92 is arranged with passages 94 through which the arms 84, 88 of the push button 82 extend. Further the ring-shaped body 76 of the release tab 74 is attached to a proximally directed surface of the end wall 92, as seen in FIG. 6. The end wall 92 of the knob 90 is arranged with a central post 95, FIG. 7, having a proximally directed support surface 96. A plunger rod drive spring 98 FIGS. 1 and 2, is arranged between the support surface 96 of the knob and a distally directed surface of an end wall 100, FIG. 2, of the plunger rod 70.

The proximal end of the knob 90 is further arranged with an outwardly directed circumferential ledge 102. The ledge 102 is designed with a zig-zag-shaped surface that is intended to cooperate with a correspondingly zig-zag-shaped surface 104, FIG. 7, on a proximally directed circumferential ledge arranged in a central passage 106 of an end cap 108 of the housing 10. The central passage 104 is arranged such that the knob 90 can extend there-through in the distal direction. The end cap 108 is attached to the housing by suitable means such as glue, welding, snap-in elements etc.

The end cap 108 is further arranged with proximally directed posts 110, which posts are arranged to come in contact with the distally directed surfaces of the support plates 52 of the medicament container holder 18. Further, a blocker plate 112 is arranged to the end cap 108, FIG. 6. It comprises a hub 114 intended to be placed in the central passage 104 and it is rotationally locked to the end plate 108 by generally radially extending tabs 116 that fit into recesses 118 on the edge of the central passage 104. The blocker plate 112 is also arranged with a central passage 120 through which the plunger rod 70 may extend. Around the circumference of the central passage 120 a number of distally directed stop ledges 122 are arranged, which are arranged to interact with the arms 78 of the release tab 74 such as to limit rotational movement of the knob 90 and the release tab 74.

The blocker plate 112 is held in position in the end cap 108 by a blocker plate nut 124. It comprises a ring-shaped body 126 arranged with thread segments 128 on its outer surface. These tread segments 128 are arranged to interact with corresponding inclined grooves 130 on an inner surface of the central passage 104 of the end cap 108. The blocker plate nut 124 is locked in position by generally circumferentially extending flexible arms 131 that fit into the recesses 118 of the end cap 108 when the blocker plate nut is in its locking position.

Figure 8:
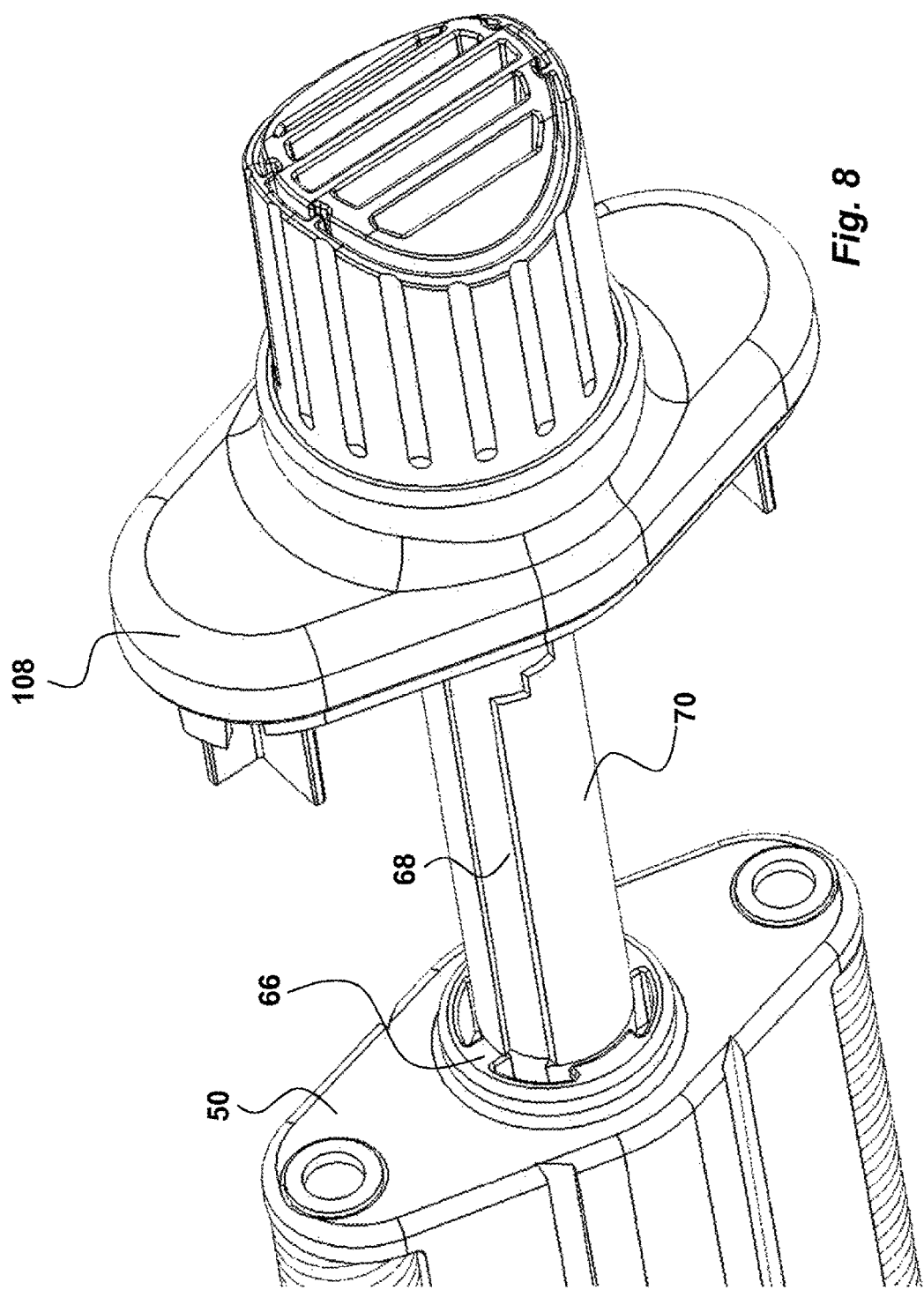
Figure 9:
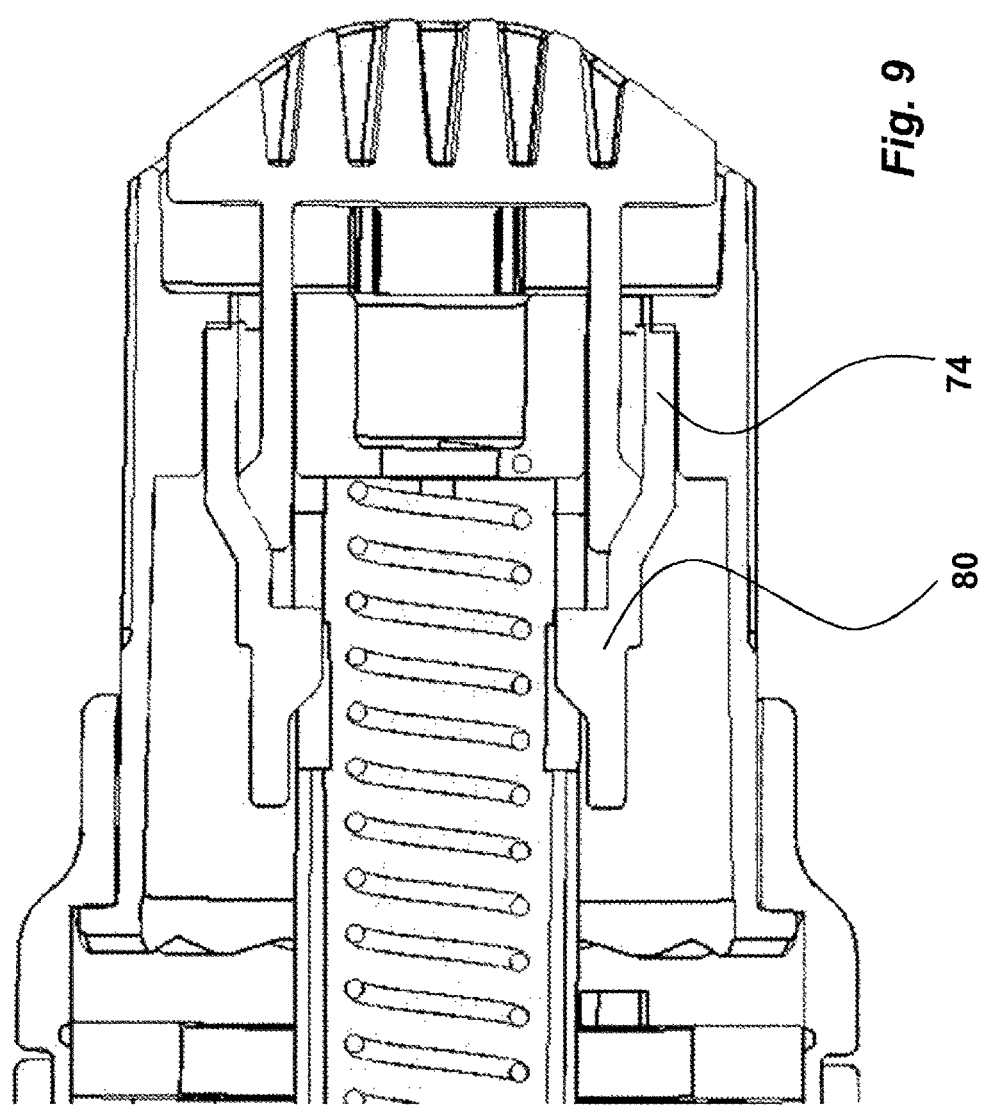

The device is intended to function as follows. The device is delivered to the user as seen in FIG. 2. The device is loaded with a medicament container 28. The medicament container holder 18 extends in the proximal direction out of the housing 10. The actuation springs 60 are compressed and the medicament container holder 18 is held in that state in relation to the housing 10 in that the ledges 64 in the central passage of the medicament container holder 18 are abutting the first stop ledges $72_I$ of the plunger rod 70 as seen in FIG. 8. The plunger rod 68 is in turn held in position by the ledges 80 of the release tab 74 being positioned in the fourth section $72_{IV}$ and abutting the fourth stop ledge $72_{IV}$ as seen in FIG. 9. The drive spring 98 of the plunger rod 70 is tensioned, as seen in FIG. 2.

Figure 10:
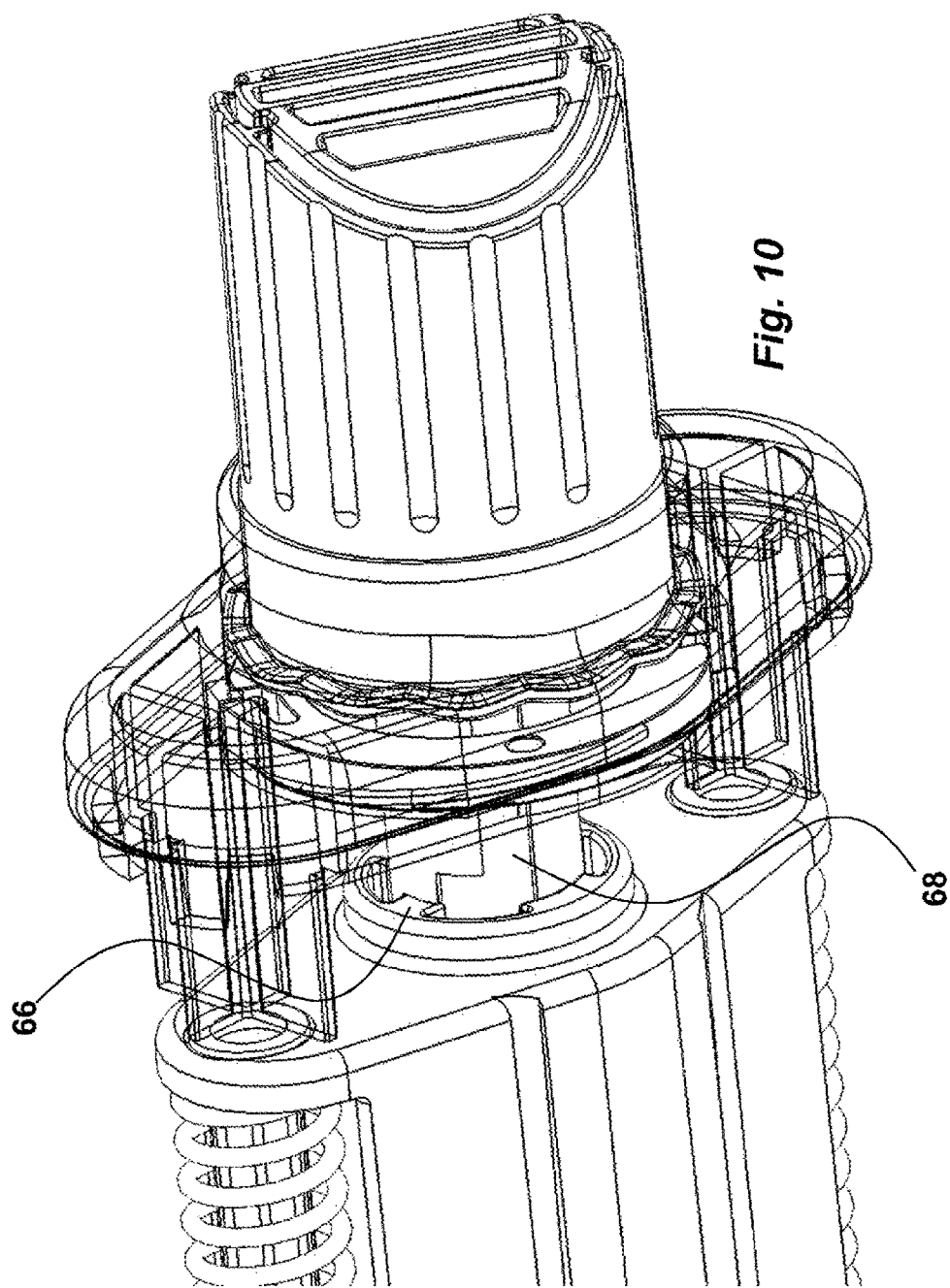
Figure 11:
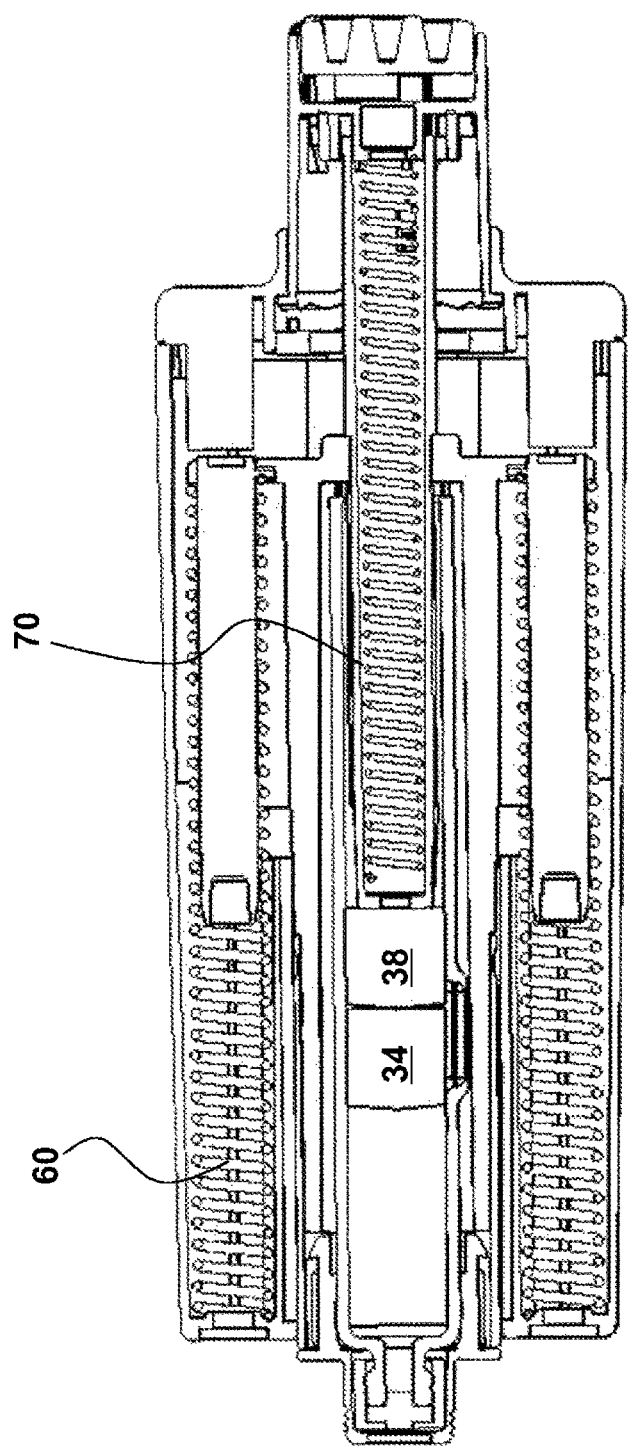

The first step is to mix the medicament and the diluent in the medicament container 28. The user then turns the knob 90 a number of steps that are caused by the zig-zag surfaces 104 between the knob 90 and the medicament container holder 18. The ledges 66 of the central passage 64 are then moved into the second section $68_{II}$ of the groove 68 plunger rod 70. The medicament container holder 18 with its medicament container 28 is now free to move in the distal direction due to the actuation springs 60. Since the plunger rod 70 is stationary it will act on the stoppers 34, 36 inside the medicament container 28 whereby the medicament will mix with the diluent. The movement is stopped when the ledges hit the second stop ledges $66_{II}$, FIGS. 10 and 11.

Figure 12:
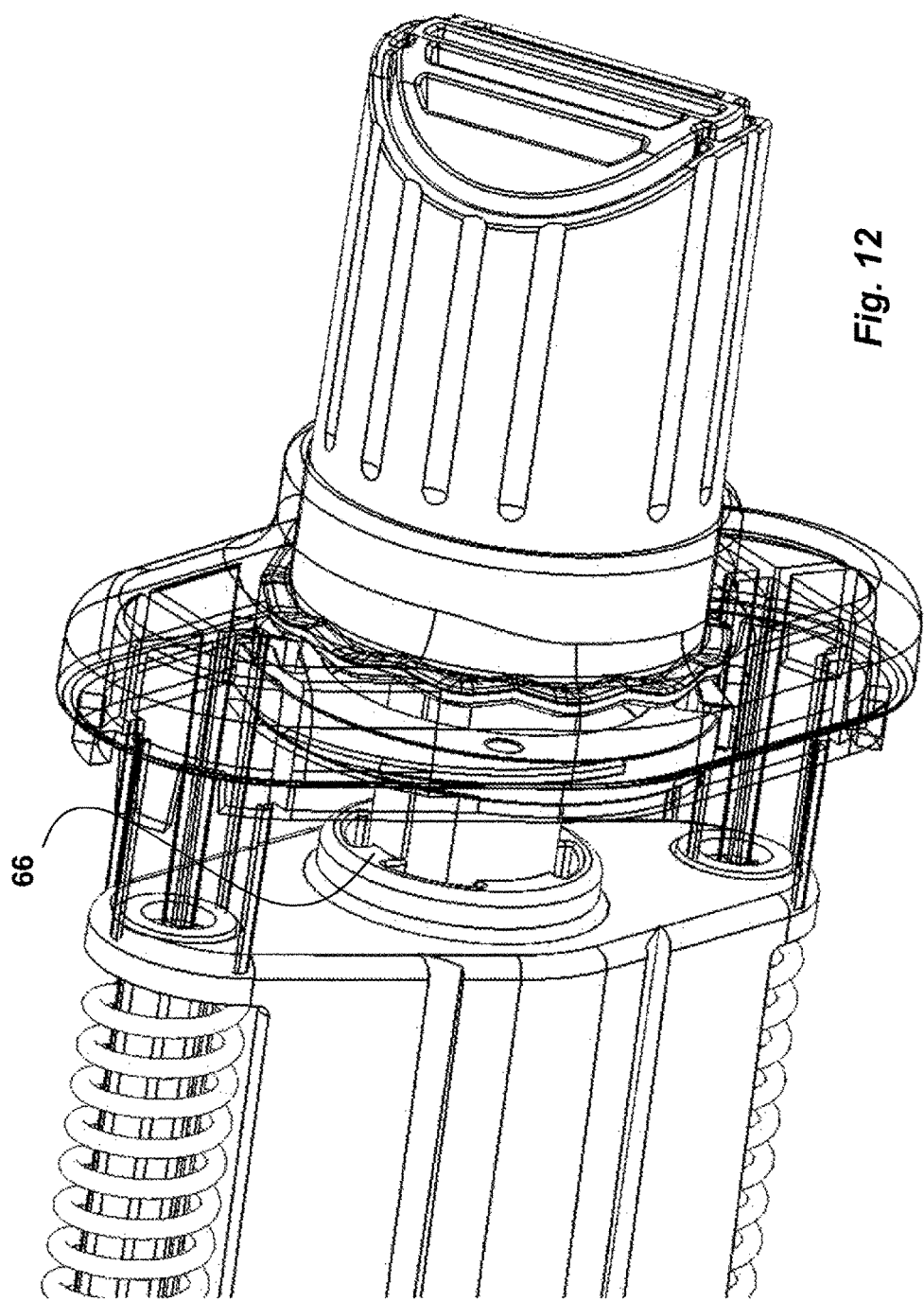

After the mixing, the user then attaches a medicament delivery member 42 to the proximally directed neck 40 of the medicament container retainer 38. In the embodiment shown an injection needle is attached. Due to the mixing, the medicament container 28 has to be primed in order to remove any air or gas trapped inside. The user then turns the knob 90 further steps, whereby the ledges 66 will enter the third section $68_{III}$ and the medicament container holder 18 and the medicament container 28 now moves the distance $d_{III}$, FIG. 12, which causes the plunger rod 70 to act on the stoppers 34, 36, thereby removing any residual air.

Figure 13:
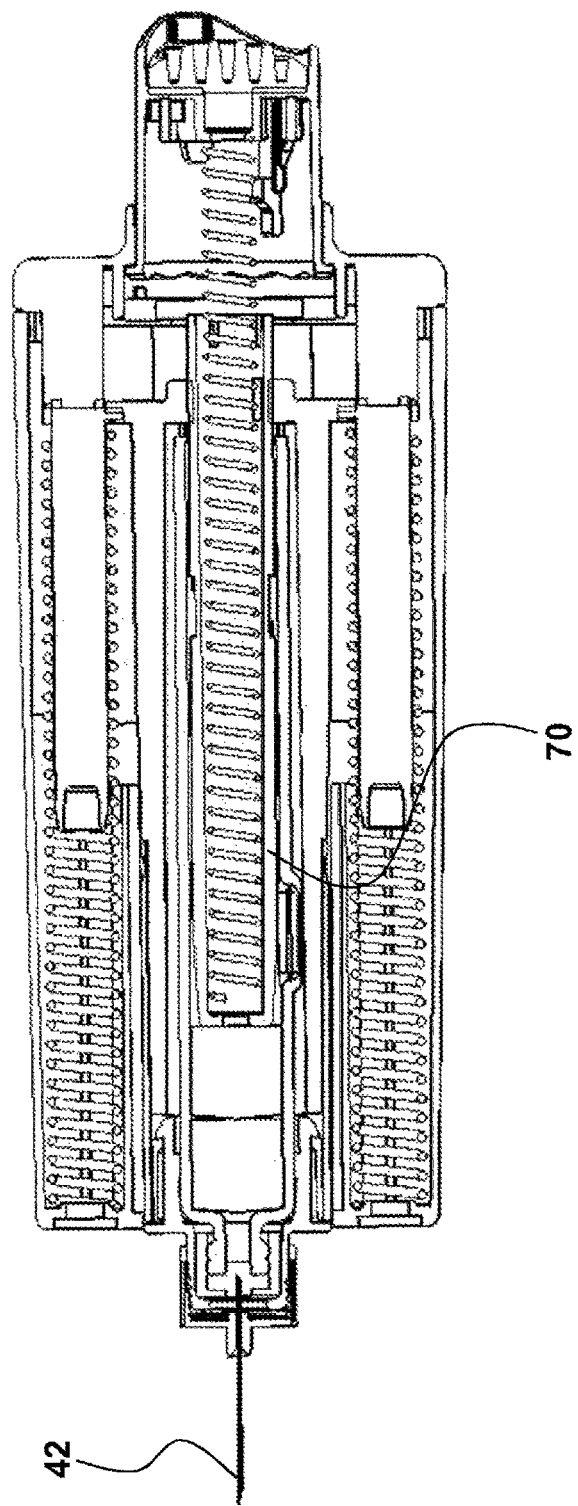

The device is now ready for delivering a dose of medicament. The user presses the proximal end of the device against a dose delivery site and in the present embodiment, a penetration is performed. In order to start the injection sequence, the knob 90 is turned further steps whereby the ledges 66 will be moved into the fourth section $68_{IV}$. However, now the medicament container holder 18 cannot move further in the distal direction because the distally directed surface of the medicament container holder 18 is in contact with the posts 110 of the end cap 108. The user therefore presses the push button 82 in the proximal direction, which causes the protrusions 86 of the arms 84 of the push button 82 to press on the arms 78 of the release tab 74 such that its ledges 80 are moved out of contact with the fourth stop ledge $72_{IV}$ of the fourth section $68_{IV}$ on the plunger rod 70. The plunger rod 70 is now urged in the proximal direction by the drive spring 98, which in turn causes the stoppers 34, 36 to be moved in the proximal direction, wherein a dose of medicament is delivered through the medicament delivery member 42, FIG. 13. When the injection sequence is completed, the device may be removed from the dose delivery site and discarded in a safe way, possibly also by removing and recapping the injection needle if such is used.

It is to be understood that the embodiment described above and shown in the drawings is to be regarded only as non-limiting examples of the invention and that it may be modified in many ways within the scope of the patent claims.

The invention claimed is:

1. A medicament delivery device comprising a housing;
   a medicament container holder arranged movable in a longitudinal direction in relation to the housing, which medicament container holder is arranged to accommodate a medicament container, which medicament container is arranged as a multi-chamber container comprising medicament and diluent in separate chambers;
   a plunger rod operably arranged to act on the medicament container;

a retainer releasably engaged with the plunger rod that holds the plunger rod axially fixed relative to the housing; and an actuation spring held in a tensioned state and positioned between the medicament container holder and the housing such that upon release of the tension in the actuation spring, the actuation spring causes the medicament container holder to move axially with the actuation spring in a distal direction relative to the housing such that said plunger rod acts on said medicament container causing mixing of said medicament and said diluent.

2. The medicament delivery device according to claim 1, further comprising a drive spring operably connected to said plunger rod such that, when said retainer is actuated for releasing said plunger rod, said plunger rod is forced to act on said medicament container for expelling the mixed medicament through a medicament delivery member.

3. The medicament delivery device according to claim 1, wherein said plunger rod comprises first stop elements co-acting with said retainer and capable of holding said plunger rod in an initial position, and wherein said plunger rod comprises second stop elements capable of stopping said plunger rod after a first distance in the longitudinal direction for performing mixing.

4. The medicament delivery device according to claim 3, wherein said plunger rod comprises third stop elements capable of stopping said plunger rod after a second distance in the longitudinal direction for performing priming.

5. The medicament delivery device according to claim 4, wherein each of the first, second and third stop elements comprise a stop ledge arranged on an outer surface of said plunger rod, where each stop ledge is arranged generally transversal to the longitudinal direction and is positioned to interact with stop surfaces on said medicament container holder.

6. The medicament delivery device according to claim 5, wherein said stop surfaces comprise fixed ledges arranged to move in longitudinally extending groove sections on the outer surface of said plunger rod.

7. The medicament delivery device according to claim 6, wherein said groove sections are placed offset to each other in a circumferential direction of said plunger rod, and wherein an end surface of a groove section comprises said stop ledges.

8. The medicament delivery device according to claim 7, wherein said plunger rod is arranged turnable in order to move said fixed ledges from one groove section to a subsequent groove section.

9. The medicament delivery device according to claim 1, wherein it further comprises a manually operable activator that is operably connected to said retainer to release said plunger rod when activated.

10. The medicament delivery device according to claim 9, wherein said retainer comprises ledges arranged to fit into a groove segment on said plunger rod and to contact a stop ledge for holding said plunger rod.

11. The medicament delivery device according to claim 10, wherein said manually operable activator comprises protrusions operably arranged to move said ledges of said retainer out of contact with said stop ledge for releasing said plunger rod.

* * * * *